United States Patent
Yamanaka et al.

(10) Patent No.: US 9,106,806 B2
(45) Date of Patent: Aug. 11, 2015

(54) IMAGE SENSING DEVICE

(71) Applicant: SANYO ELECTRIC CO., LTD., Moriguchi-shi, Osaka (JP)

(72) Inventors: Yoshitaro Yamanaka, Moriguchi (JP); Tomoyoshi Tokumaru, Moriguchi (JP); Mikio Houjou, Moriguchi (JP)

(73) Assignee: PANASONIC HEALTHCARE CO., LTD., Ehime (JP)

( * ) Notice: Subject to any disclaimer, the term of this patent is extended or adjusted under 35 U.S.C. 154(b) by 433 days.

(21) Appl. No.: 13/731,805

(22) Filed: Dec. 31, 2012

(65) Prior Publication Data

US 2013/0120552 A1 May 16, 2013

Related U.S. Application Data

(63) Continuation of application No. PCT/JP2011/066488, filed on Jul. 20, 2011.

(30) Foreign Application Priority Data

Jul. 28, 2010 (JP) .................................. 2010-169832

(51) Int. Cl.
*H04N 7/18* (2006.01)
*C12M 1/34* (2006.01)
(Continued)

(52) U.S. Cl.
CPC ................. *H04N 7/18* (2013.01); *C12M 41/46* (2013.01); *G06T 3/0075* (2013.01); *G06T 7/2033* (2013.01); *G06T 2207/10016* (2013.01); *G06T 2207/30024* (2013.01)

(58) Field of Classification Search
CPC .................... C12M 41/46; G06T 2207/10016; G06T 2207/30024; G06T 3/0075; G06T 7/2033; H04N 7/18
USPC .......................................................... 348/80
See application file for complete search history.

(56) References Cited

U.S. PATENT DOCUMENTS 5,791,345 A * 8/1998 Ishihara et al. ............... 600/368
2009/0081769 A1 3/2009 Kiyota et al.
(Continued)

FOREIGN PATENT DOCUMENTS

JP 2004-361086 A 12/2004
JP 2007-275030 A 10/2007
(Continued)

OTHER PUBLICATIONS

International Search Report issued in International Patent Application No. PCT/JP2011/066488 dated Sep. 27, 2011.

*Primary Examiner* — Behrooz Senfi
(74) *Attorney, Agent, or Firm* — McDermott Will & Emery LLP

(57) ABSTRACT

The image sensing device (1) includes: a vessel holding portion (32) that holds a culture vessel (S); a swing portion (60) in which the vessel holding portion (32) is provided; a vibration application portion (50); an image sensing portion (10) that senses an image of the cells within the culture vessel (S); an image correction portion (4) that uses images at a plurality of image sensing places which include at least one image sensed by the image sensing portion (10) during vibration so as to correct a displacement between the images caused as a result of the image sensing places being different; and an image processing portion (5) that uses the image sensed by the image sensing portion (10) and the image corrected by the image correction portion (4) so as to distinguish between a state of floatation of the cells and a state of adherence thereof.

9 Claims, 8 Drawing Sheets

(51) Int. Cl.
*G06T 7/20* (2006.01)
*G06T 3/00* (2006.01)

(56) References Cited

U.S. PATENT DOCUMENTS

2009/0143671 A1* 6/2009 Ishibashi .................. 600/424

2009/0304257 A1 12/2009 Ohjo et al.

FOREIGN PATENT DOCUMENTS

| JP | 2009-089628 A | 4/2009 |
| JP | 2009-162974 A | 7/2009 |
| WO | WO-2007/136073 A1 | 11/2007 |

* cited by examiner

FIG.13
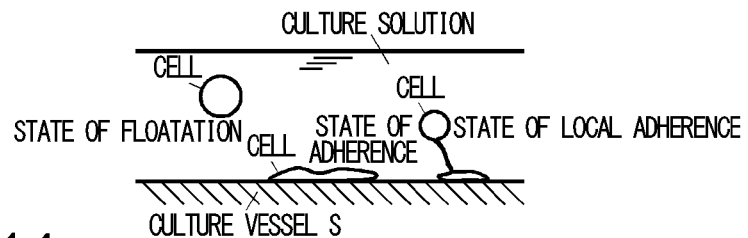
FIG.14
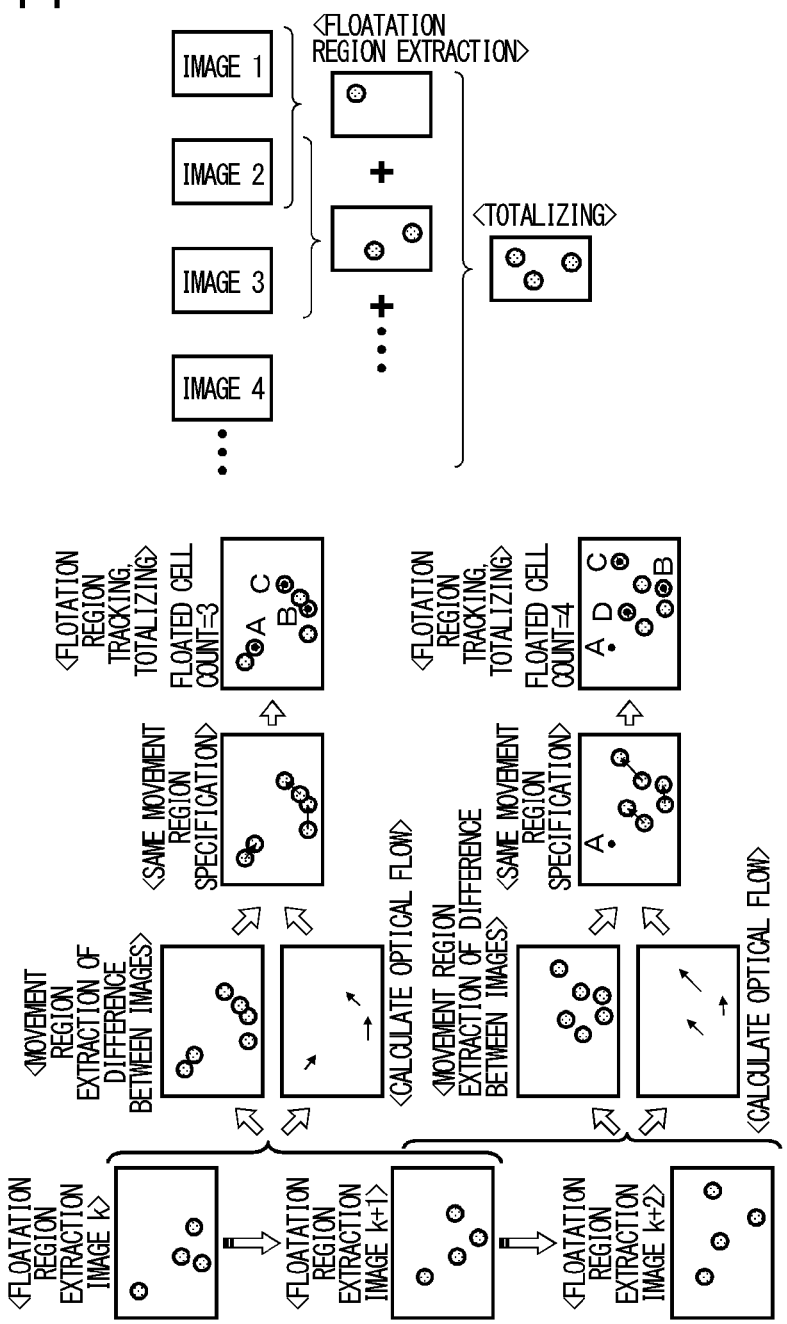
FIG.15

IMAGE SENSING DEVICE

This application is a continuation application of and claims the benefit under 35 USC 120 to International Patent Application No. PCT/JP2011/066488, filed on Jul. 20, 2011, and also claims the benefit of foreign priority of Japanese patent application No. JP2010/169832, filed on Jul. 28, 2010.

TECHNICAL FIELD

The present invention relates to an image sensing device for cells.

BACKGROUND ART

Cells are cultivated with a culture vessel such as a dish or a petri dish into which a culture solution is poured. Then, when an incubation time elapses, the culture vessel may be filled with the cells or it may be difficult for the cells to grow. Hence, passage culture may be performed in which the cultivated cells are collected and moved into a new vessel to maintain the cultivation of the cells.

In the passage culture, it is necessary to separate the cells adhered to the culture vessel; the conditions of the adherence are often different depending on variations between the individual cells. Hence, according to the conditions of the adherence of the cells to the culture vessel, it is required to adjust the number of times of washing of and the amount of flow of washing of the cells before being separated, to adjust a time up to trypsin separation and to change the force of hitting and the number of times of hitting the culture vessel in order to complete the separation operation. Hence, it is necessary to accurately determine the state of floatation of the cells in the culture solution within the culture vessel and the state of the adherence. Furthermore, when it is possible to distinguish between the state of floatation of and the state of adherence of the cells contained in the culture vessel, the graft survival after the cell dissemination in the culture vessel can be roughly estimated.

Examples of the method of distinguishing between the state of floatation of the cells in the culture solution within the culture vessel and the state of the adherence, as described above, can be found in Patent documents 1 and 2. In a recognition device disclosed in Patent document 1, a stage on which a culture vessel is placed is moved to produce convection within the culture vessel, and thus physical vibrations that cause the displacement of the cells floated within the culture vessel but does not cause the displacement of the cells adhered are provided with the result that images are sensed and analyzed. In a cell separation determination method disclosed in Patent document 2, a culture vessel placed on a vibration application stage is vibrated together with the vibration application stage and two images of a culture solution at rest and after being vibrated are sensed, and are distinguished between a state of floatation of the cells and a state of adherence thereof.

RELATED ART DOCUMENT

Patent Document

Patent document 1: JP-A-2009-89628
Patent document 2: JP-A-2007-275030

SUMMARY OF THE INVENTION

Problems to be Solved by the Invention

However, since the recognition device disclosed in Patent document 1 moves the stage on which the culture vessel is placed in order to produce convection within the culture vessel, backlash is likely to be generated between mechanical elements used for the movement of the stage. Thus, even if an image is sensed in the same position before and after the movement of the stage, the position may be displaced, with the result that there is a fear that adhered cells are erroneously determined to be floated. Furthermore, this recognition device is designed under conditions in which physical vibrations that do not displace the cells bonded (adhered) are provided, and no consideration is given to the possibility that the two images sensed before and after the movement of the stage are displaced.

In the cell separation determination method disclosed in Patent document 2, the culture vessels placed on the vibration application stage is vibrated together with the vibration application stage. But dimensional errors produced at the time of manufacturing of the culture vessel itself and clearances produced in a place where the culture vessel is attached to the vibration application stage may unintentionally cause the movement of the culture vessel. Thus, the two sensed images may be displaced, and there is a fear that the adhered cells are erroneously determined to be floated. Since, in the cell separation determination method described above, no consideration is given to the displacement of the two images, it is highly likely that the state of floatation of the cells in the culture solution cannot be appropriately distinguished from the state of the adherence thereof.

On the other hand, with respect to the state of floatation of the cells in the culture solution and the state of the adherence, it is likely that the cells are viscous, part of the cells are adhered to the culture vessel and other part thereof are floated in the culture solution. In Patent documents 1 and 2, it is highly likely that the state where the cells are locally adhered as described above cannot be distinguished from the state where the cells are completely adhered to the culture vessel. Hence, in Patent documents 1 and 2, it is likely that the state where the cells are locally adhered to the culture vessel is erroneously determined to be the state where the cells are completely adhered to the culture vessel.

The present invention is made in view of the forgoing conditions; an object of the present invention is to provide an image sensing device that uses images at a plurality of different times and that can distinguish between the state of floatation of cells in a culture solution and the state of the adherence. Another object of the present invention is to provide an image sensing device that can clearly determine that cells locally adhered to the culture vessel are floated cells.

Means for Solving the Problem

To solve the above problem, provided is an image sensing device according to the present invention including: a vessel holding portion that holds a vessel containing cells and a culture solution; a swing portion in which the vessel holding portion is provided; a vibration application portion that applies vibrations to the swing portion; an image sensing portion that senses an image of the cells contained within the vessel; an image correction portion that uses images at a plurality of image sensing places which include at least one image sensed with the image sensing portion during vibration so as to correct a displacement between the images caused as a result of the image sensing places being different; and an image processing portion that uses the image sensed with the image sensing portion and the image corrected by the image correction portion so as to distinguish between a state of floatation of the cells and a state of adherence thereof.

Since the vibration application portion applies vibrations, the places sensed by the image sensing portion at different times are generally different unless synchronization with the period of the vibrations occurs. Since the places where the images are sensed at different times are generally different from each other, the image correction portion corrects the displacement of an image target such as cells caused by the difference.

Since, in this configuration, the images at a plurality of different times including the image during the vibration are used to correct the displacement between the images, the adhered cells are prevented from being determined to be the floated cells. Furthermore, the state of the cells locally adhered to the culture vessel is distinguished from the state of the cells completely adhered to the culture vessel.

Preferably, in the image sensing device configured as described above, the image correction portion identifies the displacement between the images from a difference between a position of a first feature point in one image and a position of a second feature point, in another image, corresponding to the first feature point, and generates an image in which the displacement is corrected. In the following description, the "feature point" means, for example, a feature point on an image that can be stably detected as a result of, for example, edge detection; for example, it means a cell on an image. A feature block when an image is divided into a plurality of blocks may be assumed to be the feature point.

In this configuration, since the position where the cells are adhered is clarified, the movement of the floated cells is easily grasped.

Preferably, in the image sensing device configured as described above, the image correction portion performs, based on positions of two corresponding feature points between two images, image conversion of parallel movement and rotational movement.

In this configuration, the method of moving the image for the image conversion is changed as necessary, and thus it is possible to effectively correct the displacement between the images.

Preferably, in the image sensing device configured as described above, the image correction portion uses images at three or more different times, and tracks and totalizes a floatation region candidate of cells in an image derived from a difference between the images, in the difference so as to determine the state of floatation of the cells.

In this configuration, since it is possible to grasp the state of floatation of the cells between the successive images, even if the cells are not always moved between the images at a plurality of different times, the state of floatation of the cells is identified.

Preferably, in the image sensing device configured as described above, the swing portion is supported by an elastic member. Another member may be present between the swing portion and the elastic member.

In this configuration, since the elastic deformation of the elastic member can be utilized, it is expected that the amount of movement of cells floated within the culture vessel is relatively increased, and thus it is possible to easily distinguish between the state of floatation of the cells and the state of the adherence.

Preferably, in the image sensing device configured as described above, the vibration application portion is joined to the swing portion, and vibrates the swing portion at an amplitude lower than a displacement of the elastic member.

In this configuration, since the vibration application portion is vibrated together with the swing portion, the image sensing device can be configured such that the whole device is vibrated. Thus, it is possible to reduce the relative displacement between the culture vessel and the image sensing portion and further enhance the effect of preventing the displacement between the images at different times.

Preferably, in the image sensing device configured as described above, a stage portion that moves the vessel holding portion supported by a holder in a horizontal direction is included, and the vibration application portion vibrates the swing portion with a fulcrum present between the swing portion and the holder. The "between the swing portion and the holder" is assumed to include the "swing portion itself" and the "holder itself" In other words, the fulcrum is present at the swing portion itself, present at the holder itself, or present between the swing portion and the holder.

In this configuration, since only the swing portion having the vessel holding portion provided is vibrated, it is possible to swing the culture solution within the culture vessel with the vibration application portion having a relatively small drive force.

Preferably, in the image sensing device configured as described above, the image sensing portion is provided in the swing portion.

In this configuration, since the vessel holding portion and the image sensing portion are together provided in the swing portion, the same vibrations can be simultaneously applied to the vessel holding portion and the image sensing portion. Thus, it is possible to reduce the relative displacement between the culture vessel and the image sensing portion and further enhance the effect of preventing the displacement between the images at different times.

Preferably, in the image sensing device configured as described above, the vibration application portion is configured to be able to adjust a vibration application parameter, and a current vibration application parameter is adjusted based on a result of previous determination that is obtained with the vibration application parameter by the image processing portion.

Since it can be considered that the state of the vibrations of the cells locally adhered to the culture vessel is affected by the vibration application parameter of the vibration application portion, in this configuration, it is possible to obtain the state of the vibrations suitable for clearly determining that the cells locally adhered to the culture vessel are the floated cells.

Effects of the Invention

In the configuration of the present invention, it is possible to provide an image sensing device that uses images at a plurality of different times and thereby can accurately distinguish between the state of floatation of cells within a culture solution and the state of the adherence. It is also possible to provide an image sensing device that can clearly determine that cells locally adhered to the culture vessel are floated cells.

BRIEF DESCRIPTION OF DRAWINGS

FIG. 13 A diagram illustrating the state of floatation of the cells, the state of the adherence thereof and the state of the local adherence thereof;

FIG. 14 A diagram schematically illustrating totalizing between a plurality of images;

FIG. 15 A diagram specifically illustrating totalizing between a plurality of images;

FIG. 19 A block diagram showing the configuration of the image sensing device of

FIG. 18;

DESCRIPTION OF EMBODIMENTS

Embodiments of the present invention will be described below with reference to FIGS. 1 to 21.

First Embodiment

Figure 1:
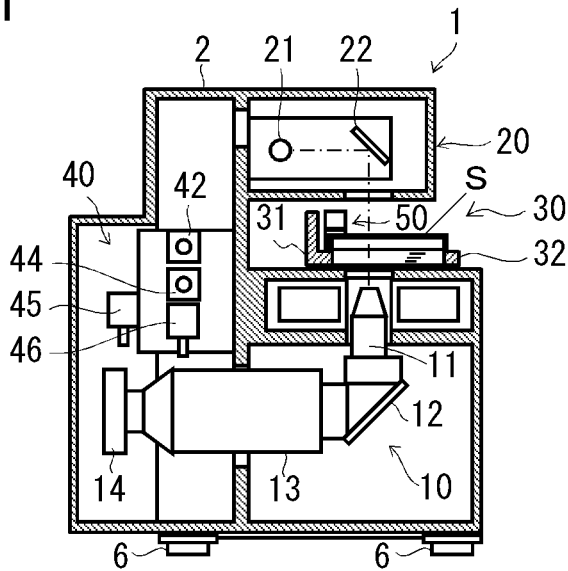
FIG. 1 A vertical cross-sectional side view of an image sensing device according to a first embodiment of the present invention.
Figure 2:
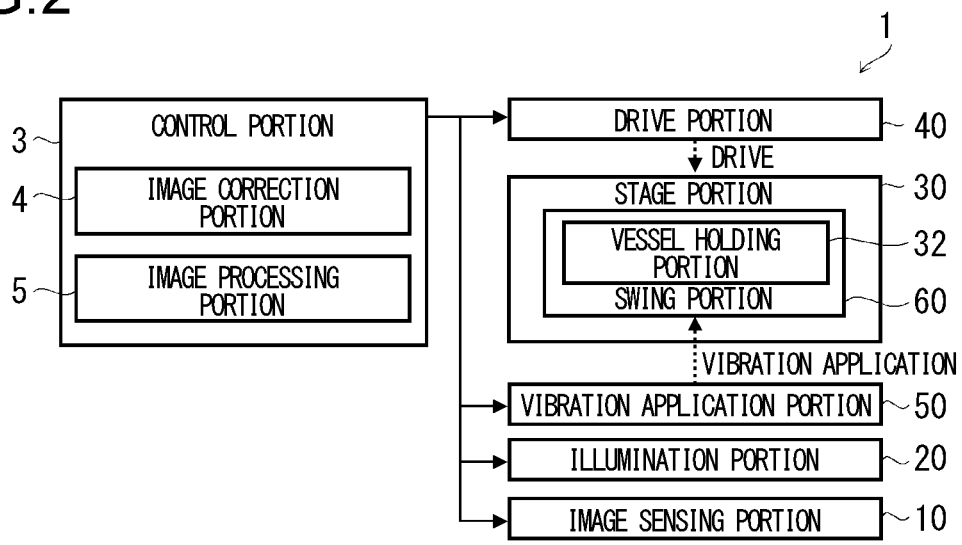
FIG. 2 A block diagram showing the configuration of the image sensing device of FIG. 1.
Figure 3:
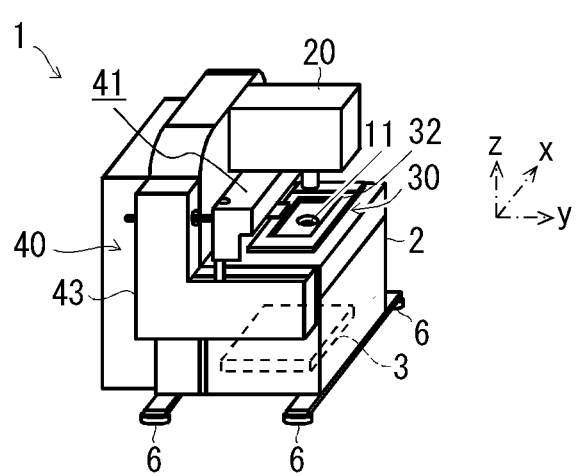
FIG. 3 A perspective view of the image sensing device of FIG. 1.
Figure 4:
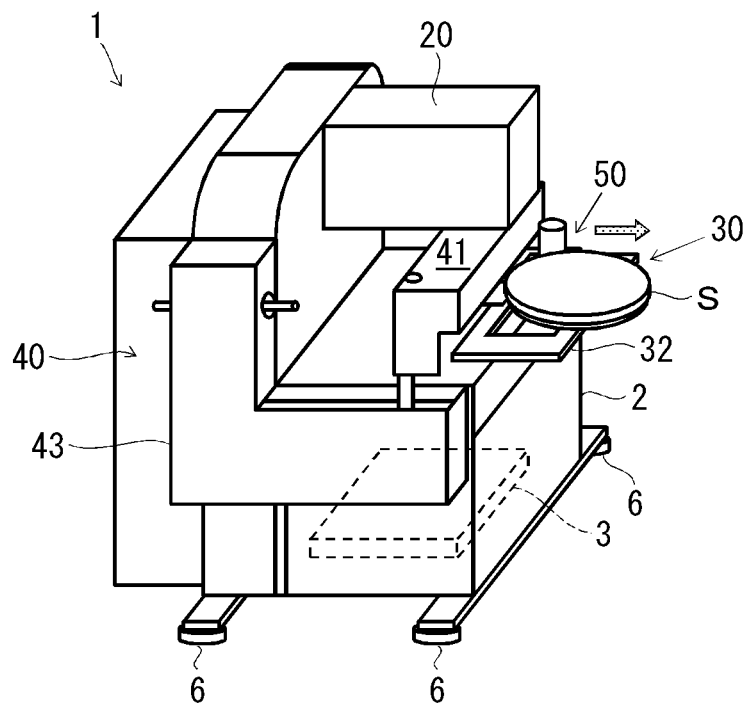
FIG. 4 A perspective view of the image sensing device similar to that of FIG. 3, showing a state where a stage portion is moved forward.

The structure of an image sensing device according to a first embodiment of the present invention will first be described with reference to FIGS. 1 to 4. FIG. 1 is a vertical cross-sectional side view of the image sensing device; FIG. 2 is a block diagram showing the configuration of the image sensing device; FIG. 3 is a perspective view of the image sensing device; FIG. 4 is a perspective view of the image sensing device, showing a state where a stage portion is moved forward. In FIG. 3, a culture vessel is omitted. In the following description, it is assumed that, in FIG. 3, the x axis direction is a left/right direction, the y axis direction is a forward/backward direction (+y direction is the forward direction and −y direction is the backward direction) and the z axis direction is an up/down direction.

As shown in FIGS. 1 to 3, the image sensing device 1 includes, in a main body 2 that is its enclosure, an image sensing portion 10, an illumination portion 20, a stage portion 30 and a drive portion 40. The image sensing device 1 can sense, with the image sensing portion 10 and the illumination portion 20, an image of cells within a culture vessel S arranged in the center portion of the front thereof, and can move, with the drive portion 40, the stage portion 30 holding the culture vessel S in a desired direction among the forward/backward direction and the left/right direction and to a desired position. The main body 2 is supported by leg portions 6 that are provided at four places to the floor surface.

The image sensing portion 10 is provided in a lower portion of the main body 2, and includes an objective lens 11, a reflective mirror 12, a zoom lens 13 and a CCD camera 14. The objective lens 11 is arranged directly below the stage portion 30 holding the culture vessel S, and is provided such that an image can be sensed upwardly. The reflective mirror 12 is arranged below the objective lens 11, and is obliquely provided such that light is reflected backward in a substantially horizontal direction. The reflective mirror 12 guides an image obtained from the objective lens 11 to the zoom lens 13 arranged backward.

The zoom lens 13 is arranged behind the reflective mirror 12, and is provided so as to extend in the forward/backward direction. The zoom lens 13 magnifies the image obtained from the objective lens 11. The CCD camera 14 is arranged further behind the zoom lens 13; the image obtained through the objective lens 11, the reflective mirror 12 and the zoom lens 13 is formed on the surface of its image sensing element. In this configuration, the image sensing portion 10 senses the image of the cells within the culture vessel S.

The illumination portion 20 is provided in an upper portion of the main body 2, and includes an LED 21 and a reflective mirror 22. The LED 21 emits light that illuminates the culture vessel S that is a target of image sensing of the stage portion 30 arranged below the illumination portion 20. The reflective mirror 22 is arranged vertically above the objective lens 11 and reflects the light emitted by the LED 21 such that the light reaches the culture vessel S and the objective lens 11.

The stage portion 30 is present in the center portion of the front of the main body 2, and is provided so as to be sandwiched between the image sensing portion 10 arranged therebelow and the illumination portion 20 arranged thereabove. The stage portion 30 holds the culture vessel S containing the cells that are the target of image sensing and the culture solution of the cells. The detailed configuration of the stage portion 30 will be described later.

The drive portion 40 is provided on the back and side of the stage portion 30, and includes an x axis drive mechanism 41, an x axis motor 42, a y axis drive mechanism 43, a y axis motor 44, a z axis motor 45 and a zoom motor 46. As shown in FIG. 3, a description will be given on the assumption that, with respect to the image sensing device 1, a left/right direction is an x axis, a forward/backward direction is a y axis and an upward/downward direction is a z axis.

The x axis drive mechanism 41 is arranged directly behind the stage portion 30, and directly supports the stage portion 30. The x axis drive mechanism 41 includes a belt, a pulley, a slide guide member and a shaft which are not shown in the figure, and is driven by the x axis motor 42 to move the stage portion 30 in the left/right direction. The y axis drive mechanism 43 is arranged on the side surfaces of the stage portion 30 and the main body 2, and supports the x axis drive mechanism 41. The y axis drive mechanism 43 includes a belt, a pulley and a slide guide member which are not shown in the figure, and is driven by the y axis motor 44 to move, together with the x axis drive mechanism 41, the stage portion 30 in the forward/backward direction (see FIG. 4).

The z axis motor 45 and the zoom motor 46 are arranged behind the stage portion 30 within the main body 2. The z axis motor 45 is a motor for moving the image sensing portion 10 in the up/down direction. The zoom motor 46 is a motor for changing the magnification of the zoom lens 13, and can change the magnification of an image to be sensed.

In order to control the overall operation of the device, the image sensing device 1 includes, as shown in FIG. 2, a control portion 3 within the image sensing device 1. The control portion 3 is formed with a general microcomputer and other electronic parts, and controls a series of operations on the image sensing device 1 based on programs and data stored and input in the microcomputer. The control portion 3 also includes an image correction portion 4 and an image processing portion 5 that correct and process an image sensed by the image sensing portion 10. The correction and processing of the image by the image correction portion 4 and the image processing portion 5 will be described in detail later.

Figure 5:
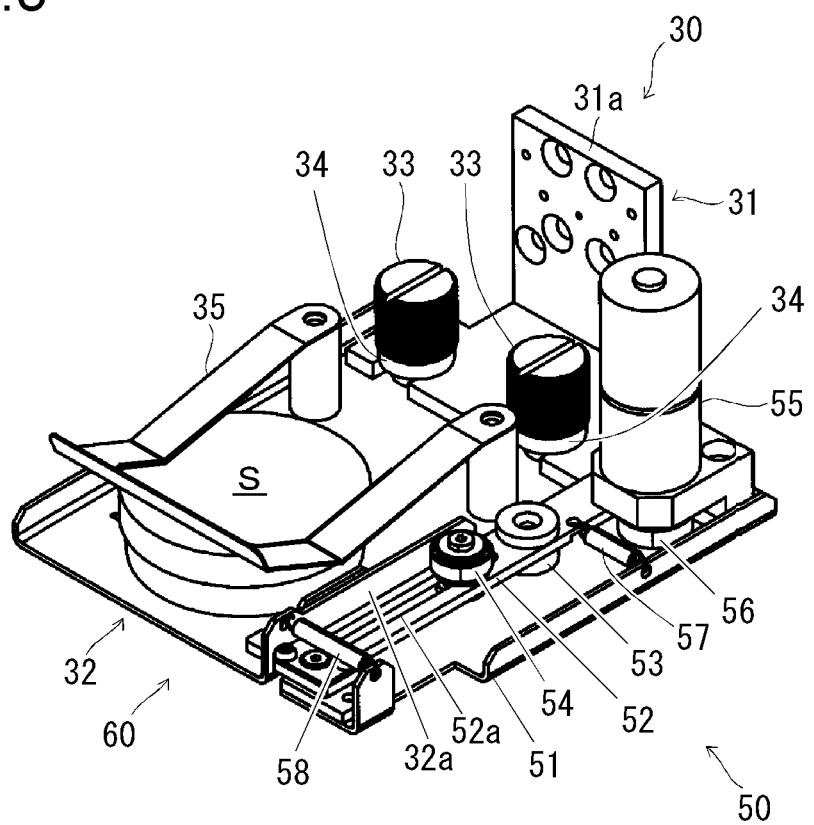
FIG. 5 A perspective view of the stage portion of the image sensing device of FIG. 1.
Figure 6:
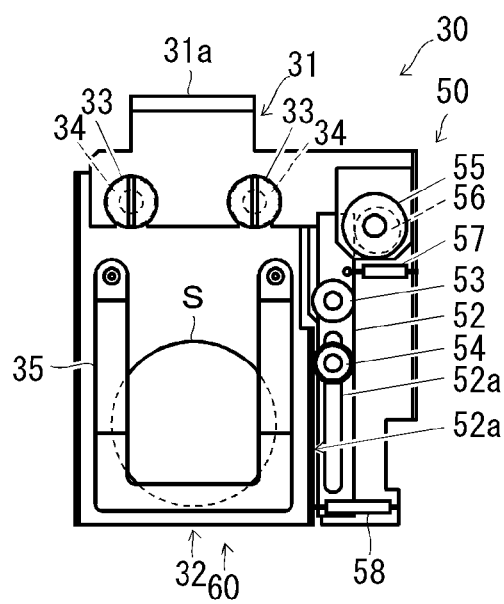
FIG. 6 A top view of the stage portion of FIG. 5.

The detailed configuration of the stage portion 30 will now be described with reference to not only FIG. 3 but also FIGS. 5 and 6. FIG. 5 is a perspective view of the stage portion 30; FIG. 6 is a top view of the stage portion 30.

As shown in FIGS. 5 and 6, the stage portion 30 includes a holder 31, a vessel holding portion 32, attachment screws 33, rubbers 34, a vessel pressing portion 35 and a vibration application portion 50.

The holder 31 is supported by the x axis drive mechanism 41 (see FIG. 3) at a support portion 31a extending substantially vertically; the holder 31 is formed in the shape of a letter L as seen from the side of the lower portion of the support portion 31a that extends horizontally toward the front. The vessel holding portion 32 is attached to the front of the holder 31 with the attachment screws 33. The rubbers 34, which are elastic members, are provided between the attachment screws 33 and the places of the holder 31 where the attachment screws 33 are screwed. In other words, the vessel holding portion 32 is supported through the rubbers 34 by the holder 31. The vessel holding portion 32 extends horizontally; the culture vessel S containing the cells and the culture solution of the cells can be placed on the upper surface thereof. The culture vessel S is pressed by the vessel pressing portion 35, which has a shape of a plate spring, such that the culture vessel S is not easily moved.

The vibration application portion 50 is positioned on the side of the vessel holding portion 32, and is attached to the holder 31. The vibration application portion 50 includes a base 51, a lever 52, a support axis 53, a contact part 54, a motor 55, an eccentric cam 56, a lever pulling spring 57 and a holding portion pulling spring 58.

The base 51 is fixed to the holder 31 at a place close to the side of the vessel holding portion 32 such that the base 51 extends forward from the holder 31. The lever 52 extends in the forward/backward direction, and is supported by the base 51 with the support axis 53. The lever 52 is supported such that it can be rotated about the support axis 53 within a horizontal plane.

The contact part 54 is provided in front of the support axis 53 of the lever 52. The contact part 54 is attached to a long hole 52a that is provided in the lever 52 so as to extend in the forward/backward direction, and its attachment place can be changed along the long hole 52a in the forward/backward direction. The contact part 54 is roller-shaped, and the side surface that is its circumferential surface is in contact with the side wall 32a of the vessel holding portion 32.

The motor 55 and the eccentric cam 56 are provided in the vicinity of an end portion of the opposite side to the side where the contact part 54 is provided with respect to the support axis 53 of the lever 52, that is, an end portion of the lever 52 on the side of the holder 31. The rotational axis line of the motor 55 extends vertically; the eccentric cam 56 is rotatably attached to the lowermost portion thereof. The rotational plane of the eccentric cam 56 extends horizontally; the side surface that is the cam-shaped circumferential surface makes contact with the lever 52. Thus, when the motor 55 is driven to rotate the eccentric cam 56, the lever 52 is swung about the support axis 53 such that its front portion, that is, the contact part 54 is displaced in the left/right direction.

The lever pulling spring 57 is provided in a place that is on the side of the eccentric cam 56 with respect to the support axis 53 of the lever 52 and that is above the base 51. Since the elastic force of the lever pulling spring 57 acts such that the lever 52 is pressed onto the eccentric cam 56, the lever 52 is constantly swung according to the cam shape of the eccentric cam 56.

As the lever 52 is swung by the drive of the motor 55 according to the cam shape of the eccentric cam 56, the contact part 54 is also swung, and the vessel holding portion 32 in contact with the contact part 54 is pressed by the contact part 54 in the left/right direction. Consequently, since the vessel holding portion 32 is supported by the holder 31 with the attachment screws 33 through the rubbers 34, the rubbers 34 are elastically deformed, and the vessel holding portion 32 is swung in the left/right direction. Since the elastic deformation of the rubbers 34 can be utilized, it is expected that the amount of movement of cells floated within the culture vessel S is relatively increased, and thus it is possible to easily distinguish between the state of floatation of and the state of adherence of the cells.

As described above, the vessel holding portion 32 serves as a swing portion 60 that is swung by the vibration application portion 50 in the left/right direction, and the vibration application portion 50 operates so as to apply vibrations to the swing portion 60. In other words, the vibration application portion 50 vibrates the swing portion 60 with fulcrums that are present in the attachment screws 33 between the swing portion 60 and the holder 31. In this way, since only the swing portion 60 having the vessel holding portion 32 is vibrated, it is possible to swing the culture solution within the culture vessel S with the vibration application portion 50 having a relatively small drive force.

Since the holding portion pulling spring 58 is provided between the vessel holding portion 32 and the base 51, and an elastic force acts such that the vessel holding portion 32 is pressed onto the contact part 54, the vessel holding portion 32 serving as the swing portion 60 is constantly swung according to the cam shape of the eccentric cam 56.

Since the position where the contact part 54 is attached is changed along the long hole 52a in the forward/backward direction, and thus it is possible to change the contact position between the contact part 54 and the vessel holding portion 32, the amplitude of the vessel holding portion 32 can be changed. In this way, the vibration application portion 50 can adjust the amplitude of the vessel holding portion 32 that is one of vibration application operation parameters. Other examples of the vibration application operation parameter include the rotational frequency of the motor 55.

Figure 7:
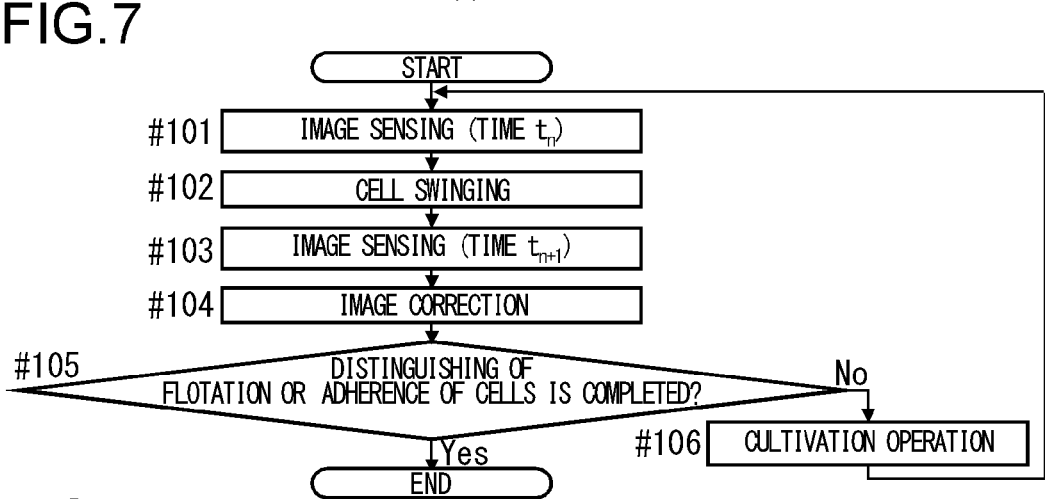
FIG. 7 A flowchart showing an operation of distinguishing, with the image sensing device of FIG. 1, between the state of floatation of cells and the state of the adherence thereof.

An operation of distinguishing, with the image sensing device 1, between the state of floatation of the cells within the culture vessel S and the state of the adherence of the cells will now be described with reference to FIG. 2 along a flow shown in FIG. 7. FIG. 7 is a flowchart showing the operation of distinguishing, with the image sensing device 1, between the state of floatation of and the state of adherence of the cells.

The operational flow shown in FIG. 7 is designed so as to expect a case where the image sensing device 1 of the present invention is incorporated in, for example, a culture device and includes the step of a "cultivation operation." The "cultivation operation" may include a manual operation performed by a person.

When the image sensing device 1 starts (start of FIG. 7) the operation of distinguishing between the state of floatation of the cells within the culture vessel S and the state of the adherence of the cells, the control portion 3 controls the image sensing portion 10 and the illumination portion 20 to first sense an image of the cells within the culture vessel S (Step #101).

Then, the control portion 3 controls the vibration application portion 50 to apply vibrations to the vessel holding portion 32 serving as the swing portion 60, and thereby swings the cells within the culture vessel S (Step #102). Then, the control portion 3 senses an image of the cells being vibrated within the culture vessel S (Step #103).

Here, the control portion 3 makes the image correction portion 4 perform an image correction (Step #104). Specifically, the image correction portion 4 uses the image of the cells at rest that is sensed in Step #101 and the image of the cells being vibrated that is sensed in Step #103 at different times to correct the displacement between the images. Thus, since the image of the cells at rest that is sensed is corrected, it is possible to prevent the adhered cells from being erroneously determined to be the floated cells.

Then, the control portion 3 makes the image processing portion 5 distinguish between the state of floatation of the cells and the state of the adherence of the cells (Step #105). Specifically, the image processing portion 5 uses the image of the cells being vibrated that is sensed in Step #103 with the image sensing portion 10 and the image of the cells at rest that is corrected in Step #104 by the image correction portion 4 to distinguish between the state of floatation of the cells and the state of the adherence.

Here, when the image sensing device 1 of the present invention is incorporated in, for example, a culture device, as a result of the distinguishing between the state of floatation of the cells and the state of the adherence of the cells, as described above, whether or not the number of floated cells is greater than a preset threshold is evaluated. If, according to the result of the evaluation, the distinguishing between the state of floatation of the cells and the state of the adherence is determined not to be completed (no in Step #105), for example, a necessary cultivation operation is added or parameters in the cultivation operation are adjusted (Step #106).

Examples of the specific cultivation operation in Step #106 include a washing operation for removing dead cells, the exchange of a culture medium and a passage culture operation of performing the separation of the adhering operation and collection. In the adjustment of parameters in the cultivation operation, for example, a washing time and the number of times of washing in the washing operation are increased or a reaction time after the addition of a separating agent and the number of times of tapping of the culture vessel after the reaction are increased.

After the cultivation operation in Step #106, the process returns again to Step #101, and the processing in Steps #101 to #105 is performed to carry out the evaluation, with the result that whether or not the distinguishing between the state of floatation of the cells and the state of the adherence is satisfactory is determined.

If, in Step #105, the distinguishing between the state of floatation of the cells and the state of the adherence is completed (yes in Step #105), the operation of distinguishing between the state of floatation of the cells and the state of the adherence of the cells is completed (end of FIG. 7).

Figure 8:
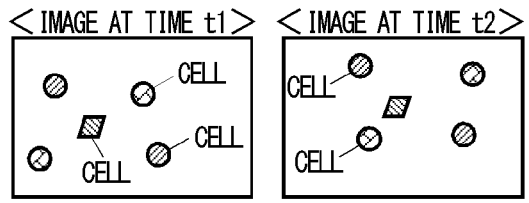
FIG. 8 A diagram illustrating an example of images sensed by the image sensing device of FIG. 1 at different times.
Figure 9:
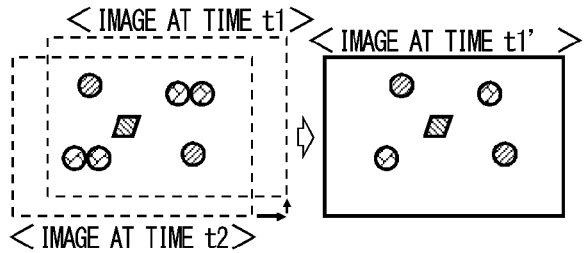
FIG. 9 A diagram illustrating a first example of a method of correcting the images of FIG. 8.
Figure 10:
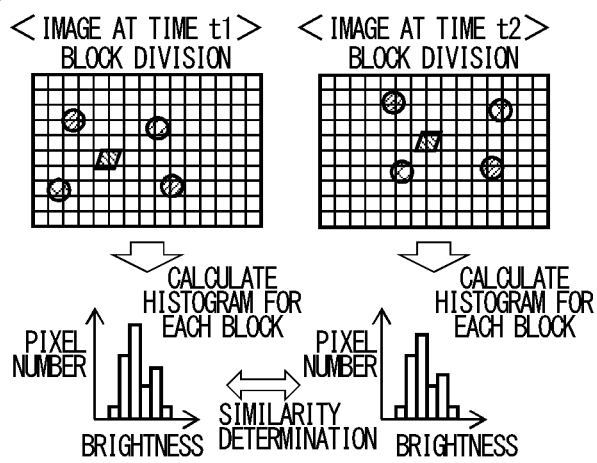
FIG. 10 A diagram illustrating a similarity distinguishment method (block matching) of the images of FIG. 8.
Figure 11:
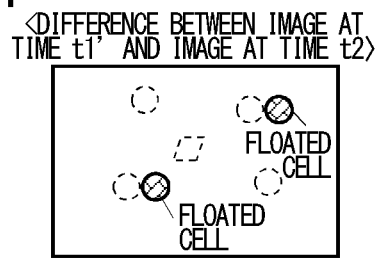
FIG. 11 A diagram illustrating a difference between the images sensed by the image sensing device of FIG. 1 at different times.
Figure 12:
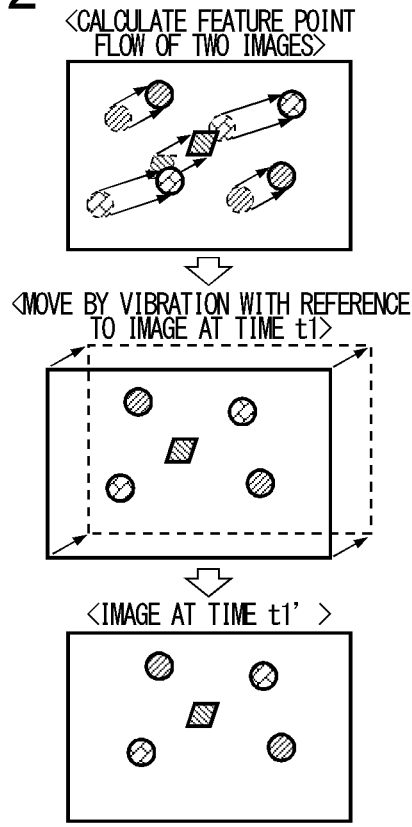
FIG. 12 A diagram illustrating a second example (optical flow) of the method of correcting the images of FIG. 8.

Subsequently, the image correction performed by the image correction portion 4 in Step #104 of FIG. 7, on the operation of distinguishing between the state of floatation of the cells and the state of the adherence, will now be described with reference to FIGS. 8 to 12. FIG. 8 is a diagram illustrating an example of images sensed by the image sensing device 1 at different times; FIG. 9 is a diagram illustrating a first example of the method of correcting the images of FIG. 8; FIG. 10 is a diagram illustrating a similarity distinguishment method (block matching) of the images of FIG. 8; FIG. 11 is a diagram illustrating a difference between the images sensed by the image sensing device 1 at different times; FIG. 12 is a diagram illustrating a second example (optical flow) of the method of correcting the images of FIG. 8.

FIG. 8 shows, as the examples of the images sensed by the image sensing device 1 at different times, an image of the culture vessel S at rest at a time t1 and an image of the culture vessel S being vibrated at a time t2. Round marks and quadrangular marks in the two images represent the cells. Since they are drawn with the assumption that a displacement occurs between the two images, all the cells appear to be moved regardless of whether they are floated or adhered. When no displacement occurs between the images, the adhered cells are not moved between the images.

On the other hand, since the vibration application portion 50 applies vibrations, the places sensed by the image sensing portion 10 at different times are generally different unless synchronization with the period of the vibrations occurs. Furthermore, even if the image sensing is performed in synchronization with the vibrations, a clearance in the structure or a backrush makes it difficult to make the sensing places completely coincide with each other. Hence, in the image at the time t1 and the image at the time t2 shown in FIG. 8, all the cells appear to be moved regardless of whether they are floated or adhered. Since the places where the images are sensed at different times are generally different from each other, the image correction portion 4 corrects the displacement of an image target to be sensed such as cells caused by the difference.

As the "displacement" described above, two types of displacement are present, that is, a displacement (observed as the displacement of the adhered cells) of the image target to be sensed caused by the difference of the places of image sensing resulting from the vibrations by the vibration application portion 50 and a displacement resulting from the vibrations of the floated cells.

As shown in FIG. 9, with reference to the image at the time t2, the image correction portion 4 converts the image at the time t1 to generate an image at a time t1' in which the displacement is corrected. Then, the image correction portion 4 identifies the displacement between the images from the difference between the position of a feature point (cells) in the image at the time t1 and the position of a feature point (cells) in the image at the time t2 corresponding to the feature point (cells) described above so as to generate images in which the displacement is corrected. The image correction portion 4 performs the image conversion of parallel movement and rotational movement based on the positions of the corresponding feature points (cells) between the two images.

With respect to the specific example of the image correction method described above, a block matching method is used as a first example, and it will be described with reference to FIG. 10. When, with reference to the image at the time t2, the image at the time t1 is converted to generate the image at the time t1' in which the displacement is corrected, the image correction portion 4 first divides the images at the time t1 and at the time t2 into blocks. Each of the blocks includes a plurality of pixels, for example, 100 pixels vertically×100 pixels horizontally.

Then, the image correction portion 4 notes a certain block where the image at the time t1 is present and calculates a histogram. In the histogram, for example, levels in the horizontal axis are the brightness of the pixels, and frequencies in the vertical axis are the number of pixels. Then, the image correction portion 4 calculates a histogram of blocks in the same position as the image at the time t2 and in the vicinity thereof, and checks similarity with the histogram of the image at the time t1. The image correction portion 4 compares the two histograms to determine their similarity.

Then, while the image correction portion 4 is slightly displacing the blocks, the image correction portion 4 repeats the comparison of the histograms of all the blocks in the images at the times t1 and t2. Here, while the image correction portion 4 is moving the blocks and the images either in parallel or rotationally, the image correction portion 4 repeats the comparison. Preferably, the size of the block is relatively roughly set at first, the comparison of the histograms is repeated while the size of the block is decreased stepwise and thus the accuracy of determination of the similarity is enhanced. Then, with reference to the image at the time t2, the position of the image at the time t1 that is determined to be most highly correlated is calculated, and, as its position information, information on the amounts of parallel movement and rotational movement is obtained.

In this way, the image correction portion 4 converts, based on the information on the amount of parallel movement and the amount of rotational movement, the image at the time t1 to correct the displacement, and generates the image at the time t1' on the right side of FIG. 9. It is found that, although the cells in the image at the time t1' are collectively moved with respect to the image at the time t1, the relative positions between the cells are not changed.

Then, by obtaining the difference between the image at the time t1' and the image at the time t2, it is possible to determine the floated cells as shown in FIG. 11.

With respect to the specific example of the image correction method of converting, with reference to the image at the time t2, the image at the time t1 to generate the image at the time t1' in which the displacement is corrected, an optical flow method is used as a second example, and it will be described with reference to FIG. 12. In this case, the image correction portion 4 first uses the images at the times t1 and t2 and calculates a feature point flow.

Then, the image correction portion 4 calculates an optical flow making the general tendency of all the cells, and regards it as the flow for the adhered cells. Since the adhered cells are not moved between the images at the times t1 and t2, the flow of the adhered cells is determined to be a displacement caused by the vibrations (displacement). Thus, the image correction portion 4 moves and corrects the image at the time t1 only by the displacement caused by the vibrations, and generates the image at the time t1' at the lower end of FIG. 12. Although, as in FIG. 9 of the block matching, in the image at the time t1', the cells are collectively moved with respect to the image at the time t1, the relative positions between the cells are not changed. Furthermore, the difference between the image at the time t1' and the image at the time t2 is obtained, and thus it is possible to determine the floated cells as shown in FIG. 11.

In the optical flow calculation processing, a flow that greatly falls outside the range is excluded by, for example, M estimation, and the average flow is calculated, with the result that a correction image may be temporarily generated. Then, the correction image and the image at the time t2 are used to calculate the optical flow. Furthermore, the generation of the correction image and the calculation of the flow using the correction image and the image at the time t2 may be repeated to improve the accuracy of the correction.

Even in the optical flow calculation processing, an image averaged for each block is temporarily generated, and the flow calculation on the image is performed, and the speed of the processing is increased by repeating the flow calculation while the size of the block is stepwise decreased, with the result that the accuracy of the correction may be enhanced.

The image at the time t2 may be corrected (converted) with reference to the image at the time t1, and the floated cells may be determined using a newly generated image at a time t2' and the image at the time t1.

Since the position where the cells are adhered is clarified through the processing performed by the image correction portion 4 described above, the movement of the floated cells is easily grasped. Then, the method of moving the image for the image conversion is changed as necessary, and thus it is possible to effectively correct the displacement between the images.

On the other hand, as shown in FIG. 13, it is likely that the cells is viscous, part of the cells are adhered to the culture vessel and other part of the cells are floated in the culture solution. FIG. 13 is a diagram illustrating the state of floatation of, the state of the adherence of and the state of the local adherence of the cells. In the state of the local adherence described above, the cells may be present in the same position between the two images, and thus there is a possibility that it is impossible to determine the state of the floatation. Hence, in order to overcome this problem, a method called "totalizing between a plurality of images" is applied in which a plurality of images including images sensed during the vibration are used, and the determination results are totalized.

Figure 16:
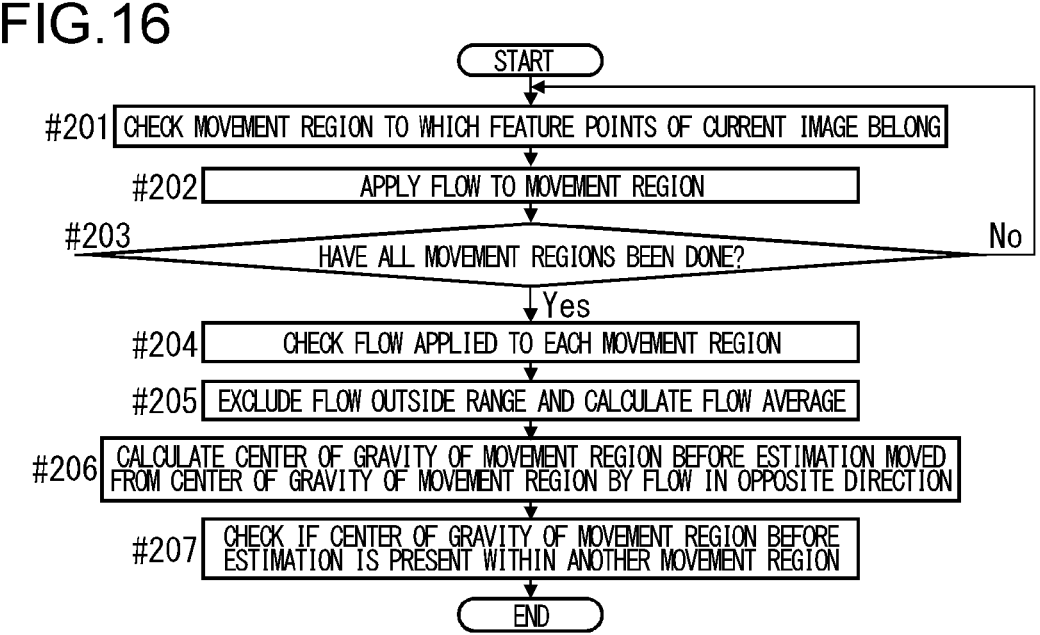
FIG. 16 A flowchart showing an operation of identifying the same movement region between images at different times in the illustrating diagram of FIG. 15.
Figure 17:
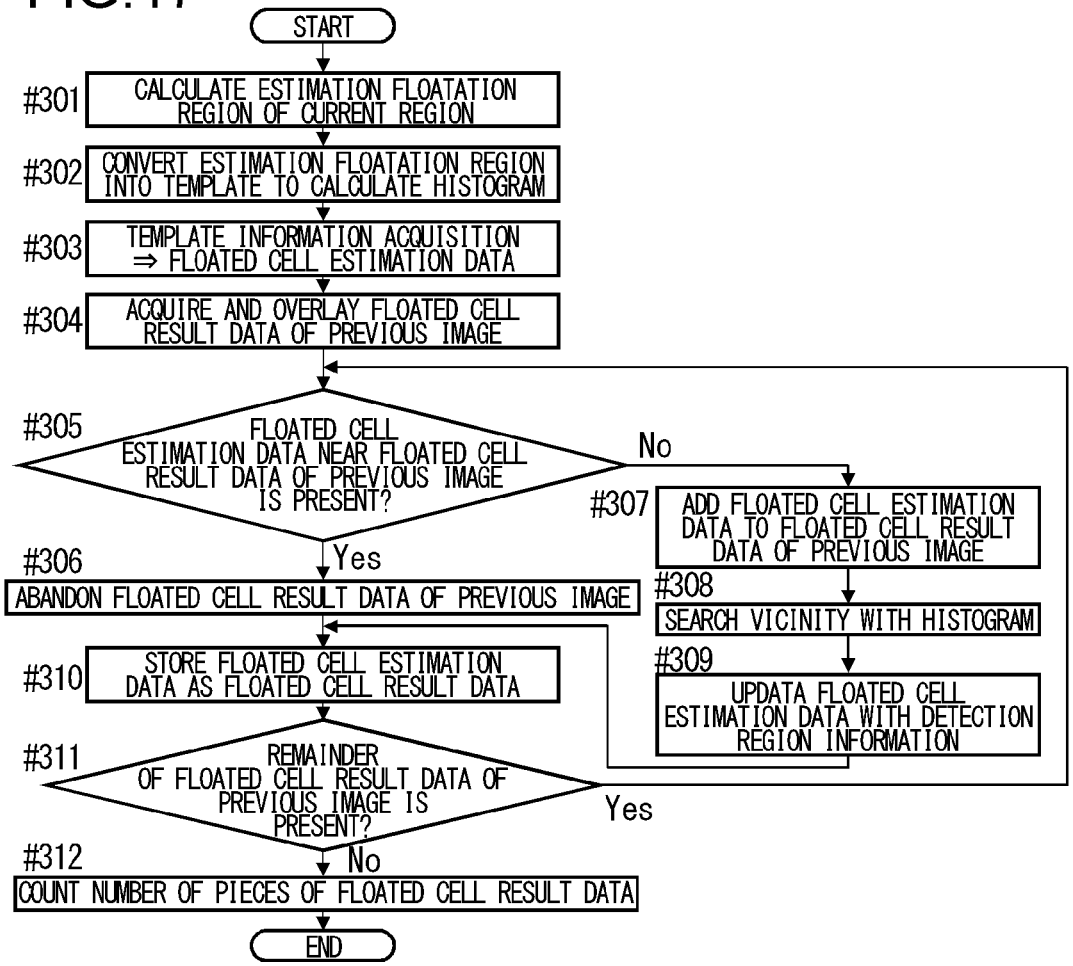
FIG. 17 A flowchart showing an operation of tracking and totalizing a floatation region in the illustrating diagram of FIG. 15.

Then, the totalizing between a plurality of images, which is the method of determining the state of the local adherence of the cells, will be described with reference to FIGS. 14 to 17. FIG. 14 is a schematic diagram illustrating the totalizing between a plurality of images; FIG. 15 is a detailed diagram illustrating the totalizing between a plurality of images; FIG. 16 is a flowchart showing an operation of identifying the same movement region between images at different times in the illustrating diagram of FIG. 15; FIG. 17 is a flowchart showing an operation of tracking and totalizing a floatation region in the illustrating diagram of FIG. 15.

In the totalizing between a plurality of images, as shown in FIG. 14, the image processing portion 5 extracts, from a plurality of images (images 1 to 4 and the subsequent images) including the images sensed during the vibration, the regions (floatation regions, represented by round marks in FIG. 14) determined to be floated as a result of the method of determining the floated cells illustrated with reference to FIGS. 7 to 13. Furthermore, the image processing portion 5 totalizes the images obtained by extracting the floatation regions. In this way, it is not necessary to synchronize the timings of the image sensing and the swinging, and thus it is possible to obtain the result of the distinguishing between the state of the floatation and the state of the adherence of the cells regardless of the adherence of the cells.

The totalizing between a plurality of images will be described in further details with reference to FIG. 15 along flows shown in FIGS. 16 and 17.

As shown in FIG. 15, the image processing portion 5 uses two continuous floatation region extraction images, for example, an image k and an image k+1, and performs, with the difference between the images, the extraction of movement regions (floatation regions, represented by round marks in FIG. 15) and the calculation of the optical flow. Then, the image processing portion 5 uses the results thereof to identify the same movement region. The processing for identifying the same movement region will be described along the flow shown in FIG. 16.

The floatation region extraction images may be generated as follows. Specifically, when the image at the time t2 is corrected with reference to the image at the time t1, and thus the floated cells are determined, the image generated by the image correction portion 4 at the time t2' is assumed to be a floatation region extraction image k. Furthermore, when the image at the time t3 is corrected with reference to the image at the time t2, and thus the floated cells are determined, the image generated at the time t3', in consideration of the amount of correction used when the image at the time t2' is generated, is assumed to be a floatation region extraction image k+1. Thereafter, the amounts of correction up to the previous processing are likewise accumulated, and thus it is possible to obtain the floatation region extraction images continuous in time with reference to the position of the adhered cells at the time t1.

When the image processing portion 5 starts (start of FIG. 16) the processing for identifying the same movement region, the image processing portion 5 checks a movement region belonging to the feature point of the current image (Step #201). Then, the image processing portion 5 applies the optical flow to the checked movement region (Step #202). Then, the image processing portion 5 determines whether or not the application of the optical flow to all the movement regions is completed (Step #203). If the application of the optical flow to all the movement regions is not completed (no in Step #203), the image processing portion 5 repeats the processing in Steps #201 and #202.

If the application of the optical flow to all the movement regions is completed (yes in Step #203), the image processing portion 5 checks the flow applied to each of the movement regions (Step #204), excludes the flow that relatively greatly falls outside the range to become noticeable and calculates the average of the flows (Step #205).

Then, the image processing portion 5 moves, by the average of the flows, in an opposite direction from the center of gravity of the movement region, and calculates the center of gravity of the movement region before estimation in the previous image (Step #206). Then, the image processing portion 5 checks whether the center of gravity of the movement region before estimation is present within another movement region (Step #207). If the center of gravity of the movement region before estimation is present within the another movement region, the image processing portion 5 determines that the movement regions are the same movement region between the images, and completes the processing for identifying the same movement region (end of FIG. 16).

With reference back to FIG. 15, when the image processing portion 5 completes the identifying of the same movement region, the image processing portion 5 assumes that the movement regions are estimation floatation regions, and tracks and totalizes the estimation floatation regions. The "tracking" means that the movement destinations of the images further subsequent in time to the estimation floatation regions identified to be the same movement region between the images are tracked. The processing for tracking and totalizing the estimation floatation regions will be described along the flow shown in FIG. 17.

When the image processing portion 5 starts the processing for tracking and totalizing the estimation floatation regions (start of FIG. 17), the image processing portion 5 calculates the estimation floatation regions of the current image (Step #301). This Step #301 means the processing described in the flow of FIG. 16. The "current image" means two continuous floatation region extraction images in FIG. 15, for example, the image k+1 in the case of the image k and the image k+1. The image k means the "previous image", which will be described later.

Then, the image processing portion 5 converts the estimation floatation regions of the current image into a template, and calculates a histogram (Step #302). Furthermore, the image processing portion 5 acquires, in addition to the histogram, template information such as a region position and a region size obtained from the estimation floatation regions of the current image, and assumes that it is floated cell estimation data (Step #303). The floated cell estimation data is composed of the region position, the region size and the histogram obtained from the estimation floatation regions; a plurality of pieces of floated cell estimation data are present according to the number of estimation floatation regions.

Then, the image processing portion 5 acquires floated cell result data on the previous image (Step #304). The floated cell result data is composed of, as a result of a series of processing steps on the previous image, the region position, the region size and the histogram obtained from the regions counted as the floated cells; a plurality of pieces of floated cell result data are present such that the number thereof is equal to the number of regions counted as the floated cells. The image processing portion 5 superimposes the floated cell result data on the floated cell estimation data.

Then, the image processing portion 5 determines whether or not the floated cell estimation data is present in the vicinity of the floated cell result data (Step #305). The range of the "vicinity" is calculated from, for example, the maximum size of the optical flow that has been observed so far or is determined from the amplitude of the vibration application operation parameter set when the vibration application portion 50 is used to apply vibrations to the swing portion 60.

If the floated cell estimation data is present in the vicinity of the floated cell result data (yes in Step #305), the image processing portion 5 abandons the floated cell result data on the previous image (Step #306). Specifically, the image processing portion 5 assumes that the floated cells are moved from the position of the previous image to the position of the current image, and leaves the floated cell estimation data on the current image.

On the other hand, if the floated cell estimation data is not present in the vicinity of the floated cell result data (no in Step #305), the image processing portion 5 adds the floated cell result data on the previous image to the floated cell estimation data without being processed (Step #307). In other words, the image processing portion 5 leaves the floated cell result data in order to cope with the case where the floated cells which are detected in the previous image are not detected in the current image.

After Step #307, the image processing portion 5 generates a histogram on the movement regions of the floated cells of the previous image, and searches, with the histogram, the vicinity thereof to track the movement regions (Step #308). The range of the "vicinity" is calculated from, for example, the maximum size of the optical flow that has been observed so far or is determined from the amplitude of the vibration application operation parameter set when the vibration application portion 50 is used to apply vibrations to the swing portion 60. Then, the image processing portion 5 updates the floated cell estimation data added in Step #307 (Step #309) using region information detected in Step #308.

Then, the image processing portion 5 stores the floated cell estimation data on the current image left in Step #306 and the floated cell estimation data updated in Step #309 as the floated cell result data on the current image (Step #301). Then, if the floated cell result data on the previous image is left (yes in Step #311), the process returns to Step #305, and the image processing portion 5 repeats the processing in Step #305 to #310.

If, in Step #311, the floated cell result data on the previous image is not left (no in Step #311), the image processing portion 5 counts the floated cell result data on the current image and assumes that the result is the number of floated cells (Step #312). Then, the processing for tracking and totalizing the estimation floatation regions is completed (end of FIG. 17). The floated cell result data on the current image is utilized, as the "floated cell result data on the previous image" in the subsequent processing for tracking and totalizing the estimation floatation region.

With reference back to FIG. 15 again, the image processing portion 5 counts the floated cells after tracking and totalizing the estimation floatation regions as described above. Specifically, in the example of FIG. 15, three cells, namely, a cell A, a cell B and a cell C, are counted regarding the floatation region extraction image k and the image k+1.

Then, as shown in FIG. 15, the image processing portion 5 performs the same processing between the floatation region extraction image k+1 and the image k+2. Here, when a feature point which is assumed to be moved between the image k and the image k+1 and a feature point which is the start point of the optical flow calculated between the image k+1 and the image k+2 are present in the same region, the image processing portion 5 determines that they belong to the movement of the same cell. In other words, in the example of FIG. 15, the cell B and the cell C correspond to what has been described above.

On the other hand, the feature point which is detected between the image k and the image k+1 determined not to be moved as described above is continuously included in the following counting of the floated cells because it is not moved between the image k+1 and the image k+2. In other words, in the example of FIG. 15, the cell A corresponds to what has been described above. A cell D is a cell that is newly determined to be floated between the floatation region extraction image k+1 and the image k+2.

Finally, between the three images, that is, the floatation region extraction image k, the image k+1 and the image k+2, the image processing portion 5 determines that the four cells, that is, the cells A to D are floated.

Based on the result of the previous determination by the image processing portion 5 obtained by using the vibration application operation parameter of the vibration application portion 50, the vibration application operation parameter when vibrations are currently produced by the vibration application portion 50 may be adjusted. Specifically, during the repetition processing in the flow of FIG. 17, it is also possible to adjust the vibration application operation parameter. An example of the result of the determination by the image processing portion 5 is the number of floated cells and the amplitude of the floated cell. An example of the vibration application operation parameter is the rotational frequency of the motor 55 and the amplitude of the swing portion 60.

Although the state of the vibrations of the cells locally adhered to the floated cells and the culture vessel S is not known, it can be considered that the state of the vibrations is changed by being affected by the adjustment of the vibration application operation parameter. For example, since, in the image processing for distinguishing between the state of the adherence of the cells and the state of the floatation, the vibration frequency of the cells is preferably low with respect to the sampling rate of the image so that, for example, the amplitude of the cells is suitable for the resolution of the image, in order for the state of the vibrations described above to be obtained, based on the result of the previous determination, the vibration application parameter for the current vibrations is adjusted.

When the vibration application parameter with which it is possible to detect a larger number of floated cells in the same sample is found, its setting is suitable for the determination of the floated cells. Every time the sample is changed or the observed point differs even in the same sample, the current setting of the vibration application parameter is preferably adjusted based on the result of the previous determination.

Since it can be considered that, as described above, the state of the vibrations of the cells locally adhered to the culture vessel S is affected by the rotational frequency of the motor 55 and the amplitude of the swing portion 60, the vibration application parameter is adjusted, and thus it is possible to obtain the state of the vibrations suitable for clearly determining that the cells locally adhered to the culture vessel S are the floated cells.

Since, as in the embodiment described above, the images at a plurality of different times including the image during the vibration are used to correct the displacement between the images, the state of the cells locally adhered to the culture vessel is distinguished from the state of the cells completely adhered to the culture vessel.

In the configuration of the embodiment of the present invention, it is possible to provide the image sensing device 1 that can accurately distinguish, with the images at a plurality of different times, between the state of floatation of the cells in the culture solution within the culture vessel S and the state of the adherence. It is also possible to provide the image sensing device 1 that can clearly determine the cells locally adhered to the culture vessel S as the floated cells.

Second Embodiment

Figure 18:
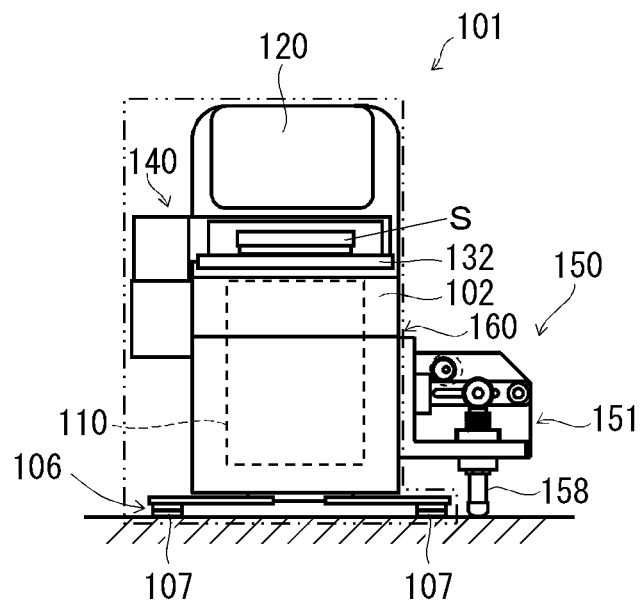
FIG. 18 A front view of the image sensing device according to a second embodiment of the present invention.
Figure 19:
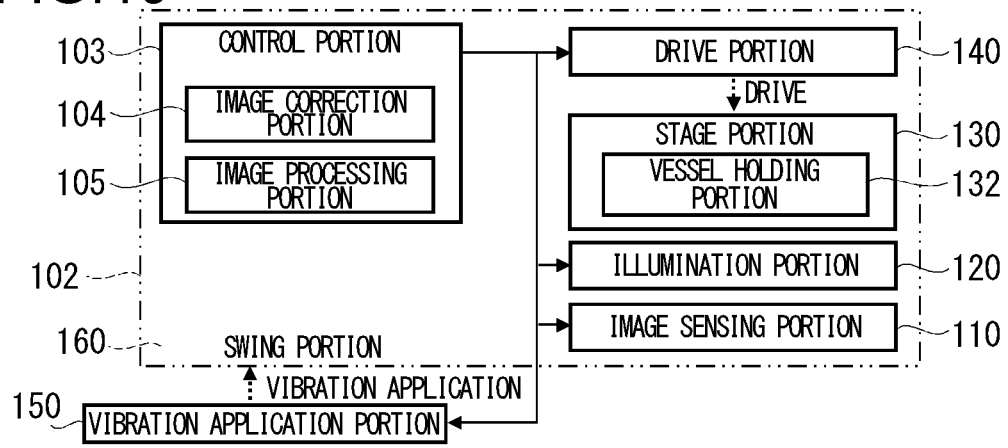
Figure 20:
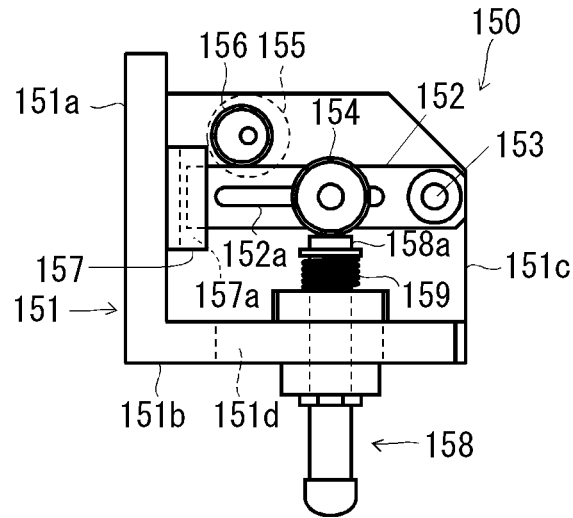
FIG. 20 A front view of an vibration application portion of the image sensing device of FIG. 18.
Figure 21:
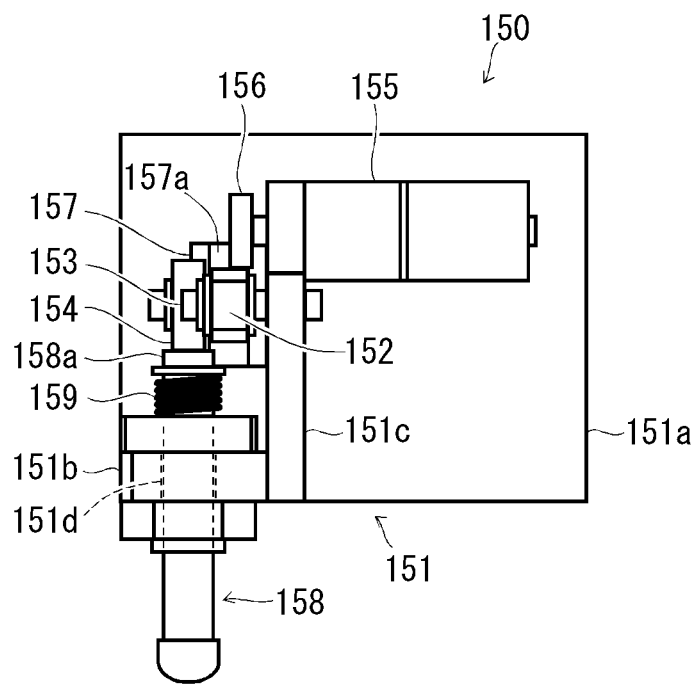
FIG. 21 A side view of the vibration application portion.

The structure of an image sensing device according to a second embodiment of the present invention will now be described with reference to FIGS. 18 and 21. FIG. 18 is a front view of the image sensing device; FIG. 19 is a block diagram showing the configuration of the image sensing device; FIG. 20 is a front view of the vibration application portion of the image sensing device; FIG. 21 is a side view of the vibration application portion. Since the basic configuration of this embodiment is the same as that of the first embodiment described with reference to FIGS. 1 to 17, in the same configuration as in the first embodiment, its depiction in the figures and its description will not be repeated.

In the image sensing device 101 of the second embodiment, as shown in FIG. 18, its main body 102 is supported by a leg portion 106 having elastic leg portion rubbers 107 provided at four places to the floor surface. Furthermore, the main body 102 has a vibration application portion 150 joined to the side surface thereof. As shown in FIGS. 18 and 19, the vibration application portion 150 vibrates, as a swing portion 160, the main body 102 supported by the leg portion rubbers 107.

As shown in FIGS. 20 and 21, the vibration application portion 150 includes a base 151, a lever 152, a support axis 153, a contact part 154, a motor 155, an eccentric cam 156, a slide guide 157, a pusher 158 and a pusher spring 159.

The base 151 includes a vertical portion 151a and a horizontal portion 151b extending in the forward/backward direction, and is formed with a plate-shaped member that is formed in the shape of a letter L as seen from the front. The vibration application portion 150 is joined to the main body 102 at the vertical portion 151a of the base 151. The base 151 is also formed with a vertical wall extending in the left/right direction, and includes a reinforcement portion 151c that couples to the vertical portion 151a and the horizontal portion 151b to reinforce the configuration thereof.

The lever 152 extends in the left/right direction, and is supported by the reinforcement portion 151c of the base 151 at the support axis 153. The support axis 153 is provided at an end portion on the outermost side of the lever 152. The lever 152 is rotatably supported about the support axis 153 within the vertical plane.

The contact part 154 is provided inward with respect to the support axis 153 of the lever 152, that is, at a place on the side of the main body 102. The contact part 154 is attached to a long hole 152a that is provided in the lever 152 so as to extend in the left/right direction, and its attachment place can be changed along the long hole 152a in the left/right direction. The contact part 154 is roller-shaped, and the side surface that is its circumferential surface is brought into contact with the upper end portion 158a of the pusher 158 arranged below the contact part 154.

The motor 155 and the eccentric cam 156 are provided at an end portion on the opposite side to the side where the support axis 153 of the lever 152 is provided, that is, they are provided in the vicinity of an end portion on the side of the main body 102. In the motor 155, its rotational axis line extends horizontally in the forward/backward direction, and is fixed to the reinforcement portion 151c; the eccentric cam 156 is rotatably attached to the forefront thereof. In the eccentric cam 156, its rotational plane extends vertically, and the side surface that is its circumferential surface having a cam shape is brought into contact with the upper surface of the lever 152. Thus, when the motor 155 is driven to rotate the eccentric cam 156, the lever 152 swings about the support axis 153 such that the side of the main body 102, that is, the contact part 154 is displaced in the up/down direction.

The slide guide 157 is provided at the vertical portion 151a arranged at a side end portion of the main body 102 of the lever 152. The side end portion of the main body 102 of the lever 152 is placed within a guide groove 157a extending in the up/down direction of the slide guide 157. In this way, the slide guide 157 is guided such that the lever 152 can be moved only in the up/down direction, and thus its movement in the forward/backward direction is limited.

The pusher 158 is arranged below the contact part 154. The pusher 158 penetrates the horizontal portion 151b of the base 151 and extends in the up/down direction. The upper end portion 158a thereof is in contact with the contact part 154; the lower end portion thereof is in contact with the floor surface. The pusher 158 is attached to a long hole 151d that is provided in the horizontal portion 151b so as to extend in the left/right direction; the place of the attachment can be changed along the long hole 151d in the left/right direction.

The pusher spring 159 is provided between the upper end portion 158a of the pusher 158 and the upper surface of the horizontal portion 151b. Since the elastic force of the pusher spring 159 acts such that the upper end portion 158a of the pusher 158 is pressed onto the contact part 154 and that furthermore the lever 152 is pressed onto the eccentric cam 156, the pusher 158 and the lever 152 are constantly swung according to the cam shape of the eccentric cam 156.

When the drive of the motor 155 causes the lever 152 to be swung according to the cam shape of the eccentric cam 156, the contact part 154 is also swung, and thus the upper end portion 158a of the pusher 158 in contact with the contact part 154 and the horizontal portion 151b of the base 151 are pressed through the pusher spring 159 in the up/down direction. Consequently, since the main body 102 in contact with the base 151 is supported by the leg portion rubbers 107, the leg portion rubbers 107 are elastically deformed, and the main body 102 is also swung in the left/right direction.

In this way, the vibration application portion 150 is joined to the main body 102, which is the swing portion 160, and is operated so as to apply vibrations to the main body 102. Here, the vibration application portion 150 applies vibrations having an amplitude lower than the displacement of the leg portion rubbers 107 provided in the leg portion 106 of the image sensing device 101. Thus, since the vibration application portion 150 is vibrated together with the swing portion 160, the image sensing device 101 can be configured such that the whole device is vibrated.

Since an image sensing portion 110 is provided in the swing portion 160, and thus a vessel holding portion 132 and the image sensing portion 110 are together provided in the swing portion 160, the same vibrations can be simultaneously applied to the vessel holding portion 132 and the image sensing portion 110. Thus, it is possible to reduce the relative displacement between the culture vessel S and the image sensing portion 110 and further enhance the effect of preventing the displacement between the images at different times.

Since the position of the attachment of the contact part 154 is changed along the long hole 152a in the left/right direction, and simultaneously, the position of the attachment of the pusher 158 is changed along the long hole 151d in the left/right direction and thus the relative positions of the main body 102 and the pusher 158 can be changed, it is possible to change the amplitude of the main body 102. In this way, the vibration application portion 150 can adjust the amplitude of the main body 102, which is one of the vibration application parameters.

Although the embodiments of the present invention have been described above, the scope of the present invention is not limited to these embodiments, and many modifications are possible without departing from the spirit of the present invention.

For example, although, in the determination of the state of the local adherence of the cells, the results of the determination using the three floatation region extraction images, that is, the image k, the image k+1 and the image k+2 in FIG. 15 are totalized, the number of images is not limited to three. Two or four or more images may be used.

The rubbers 34, which are the elastic members supporting the swing portion 60 in the first embodiment, and the leg portion rubbers 107, which are the elastic members supporting the swing portion 160 in the second embodiment, may be omitted. The elastic members are not limited to rubbers; they may be springs or sponges.

When the image sensing device 1 of the present invention is incorporated in, for example, the culture device, as a result of the distinguishing between the state of floatation of the cells and the state of the adherence thereof, whether or not the number of floated cells or the ratio of floated cells (the ratio of floated cells to the cells in the sample) is larger may be evaluated.

INDUSTRIAL APPLICABILITY

The present invention can be utilized in an image sensing device that distinguishes between the state of floatation of cells in a culture solution within a culture vessel and the state of the adherence.

LIST OF REFERENCE SYMBOLS 1, 100 image sensing device
2, 102 main body
3, 103 control portion
4, 104 image correction portion
5, 105 image processing portion
10, 110 image sensing portion
20, 120 illumination portion
30, 130 stage portion
31 holder
32, 132 vessel holding portion
34 rubber (elastic member)
40, 140 drive portion
50, 150 vibration application portion
60, 160 swing portion
106 leg portion
107 leg portion rubber (elastic member)
S culture vessel

The invention claimed is:

1. An image sensing device comprising:
a vessel holding portion that holds a vessel containing cells and a culture solution;
a swing portion in which the vessel holding portion is provided;
a vibration application portion that applies vibrations to the swing portion;
an image sensing portion that senses an image of the cells contained within the vessel;
an image correction portion that uses images at a plurality of image sensing places which include at least one image sensed with the image sensing portion during vibration so as to correct a displacement between the images caused as a result of the image sensing places being different; and
an image processing portion that uses the image sensed with the image sensing portion and the image corrected by the image correction portion so as to distinguish between a state of floatation of the cells and a state of adherence thereof.

2. The image sensing device of claim 1,
wherein the image correction portion identifies the displacement between the images from a difference between a position of a first feature point in one image and a position of a second feature point, in another image, corresponding to the first feature point, and generates an image in which the displacement is corrected.

3. The image sensing device of claim 1,
wherein the image correction portion performs, based on positions of two corresponding feature points between two images, image conversion of parallel movement and rotational movement.

4. The image sensing device of claim 1,
wherein the image correction portion uses images at three or more different times, and tracks and totalizes a floatation region candidate of cells in an image derived from a difference between the images, in the difference so as to determine the state of floatation of the cells.

5. The image sensing device of claim 1,
wherein the swing portion is supported by an elastic member.

6. The image sensing device of claim 5,
wherein the vibration application portion is joined to the swing portion, and vibrates the swing portion at an amplitude lower than a displacement of the elastic member.

7. The image sensing device of claim 1, further comprising:
a stage portion that moves the vessel holding portion supported by a holder in a horizontal direction,
wherein the vibration application portion vibrates the swing portion with a fulcrum present between the swing portion and the holder.

8. The image sensing device of claim 1,
wherein the image sensing portion is provided in the swing portion.

9. The image sensing device of claim 1,
wherein the vibration application portion is configured to be able to adjust a vibration application parameter,
and a current vibration application parameter is adjusted based on a result of previous determination that is obtained with the vibration application parameter by the image processing portion.

* * * * *